United States Patent [19]

Elliott et al.

[11] Patent Number: 4,618,718

[45] Date of Patent: Oct. 21, 1986

[54] PREPARATION OF TRIFLUOROETHYLAMINE

[75] Inventors: Arthur J. Elliott, Sloatsburg, N.Y.; Gary W. Astrologes, Hackensack, N.J.

[73] Assignee: Halocarbon Products Corporation, Hackensack, N.J.

[21] Appl. No.: 745,058

[22] Filed: Jun. 14, 1985

[51] Int. Cl.$^4$ ............................................. C07C 85/04
[52] U.S. Cl. ..................................... 564/481; 564/482
[58] Field of Search ................................ 564/481, 482

[56] References Cited

U.S. PATENT DOCUMENTS

| | | | |
|---|---|---|---|
| 2,348,321 | 12/1941 | Benning et al. | 564/481 |
| 3,764,626 | 10/1973 | Pivette | 564/481 |
| 3,849,496 | 11/1974 | Forster | 564/481 |
| 4,120,979 | 10/1978 | Schwarzmann et al. | 564/481 |

Primary Examiner—Charles F. Warren
Assistant Examiner—R. A. Picard
Attorney, Agent, or Firm—Sprung Horn Kramer & Woods

[57] ABSTRACT

In the reaction of a 2,2,2-trifluoroethyl halide with ammonia to produce 2,2,2-trifluoroethylamine, the improvement which comprises effecting the reaction with from about 1 to 3 moles of ammonia per mole of the trifluoroethyl halide at a temperature of about 170° to 240° C. and a pressure less than about 300 psig in the presence of a substantially anhydrous inert solvent present in at least about the same molar amount as the trifluoroethyl halide. Advantageously the temperature is from about 200° to 220° C., the pressure is at most about 250 psig, the solvent is N-methylpyrrolidone present in at least about 3 times the molar amount of the trifluoroethyl halide, and the halide is the chloride.

7 Claims, No Drawings

PREPARATION OF TRIFLUOROETHYLAMINE

The present invention relates to improvements in the known reaction of 2,2,2-trifluoroethyl halides with ammonia to produce 2,2,2-trifluoroethylamine.

Of the methods available for the commercial production of 2,2,2-trifluoroethylamine, the ammonolysis of the corresponding halides is the most convenient and economical. U.S. Pat. No. 2,348,321 discloses the reaction of 2,2,2-trifluoroethyl chloride with a four-fold excess of aqueous ammonia in a steel bomb at 185° C. for 6 hours. No yield or conversion is given. Dickey et al (Ind. Eng. Chem., Vol. 48, p209 1956) reports the same reaction using a six-fold excess of ammonia. In this case, the conversion is 100% and the isolated yield of the amine is 59%. Similarly, the bromide gave 55% yield of the amine. According to Meen and Wright (J. Org. Chem., Vol. 19, p391 1954) the reaction of 2,2,2-trifluoroethyl bromide with anhydrous ammonia in the absence of a solvent at 130°–140° C. gave 80% of the amine, isolated as the hydrochloride salt and contaminated with 5% of ammonium chloride. The above methods have limitations when applied to large scale industrial preparations. The use of ammonia at elevated temperatures causes high pressure necessitating the use of a specially constructed pressure vessel. While the employment of aqueous ammonia helps to reduce the pressure somewhat over the anhydrous method, the presence of water leads to corrosion of the vessel unless expensive, high alloy reactors are used.

It is accordingly an object of the present invention to provide a process for producing 2,2,2-trifluoroethylamine in high yield, with minimal corrosion, and without the need for costly high pressure equipment.

These and other objects and advantages have been realized in accordance with the present invention pursuant to which a 2,2,2-trifluoroethyl halide is reacted with from 1 to 3 times its molar amount of ammonia at a temperature of about 170° to 240° C. and a pressure less than about 300 psig in the presence of a substantially anhydrous inert solvent present in at least about the same molar amount as the trifluoroethyl halide.

It has been found that the use of non-aqueous solvents considerably reduces the corrosion of a stainless steel vessel relative to water. Such solvents also reduce the amount of fluoride ion generated during the reaction. Since fluoride ion cannot be added indiscriminately to waste water, its removal adds to the expense of such a process. Accordingly, the reduced production of fluoride ion in accordance with the present invention represents a further advantage.

Suitable solvents for the practice of the invention are those which under the reactions conditions are liquid and inert. Representative solvents include sulfolane but are preferably N-methylpyrrolidone and glycols and ethers thereof such as 2-(2-ethoxyethoxy)-ethanol, triethyleneglycol dimethylether, and the like.

As will be discussed more fully hereinbelow in connection with the examples, higher temperatures give rise to high pressures, as does too rapid addition of reactants. Accordingly, it is desirable to add reactants at a rate which does not permit the pressure to rise above about 250 psig, a pressure which allows the use of inexpensive vessels. Amounts of ammonia in excess of three-fold also give rise to excessive pressure build up.

As noted, for the purpose of this invention the molar ratio of the 2,2,2-trifluoroethyl halide to ammonia may be from 1:1 to 1:3, with the solvent being present in at least the same molar amount as the halide. The temperature of the reaction may be 170° C. to 240° C. The premixed reactants may be fed liquid phase to the heated solvent by any method which maintains the desired pressure. The pressure of the reaction may be varied depending on the pressure rating of the vessel used. In order to maintain a reaction pressure at or around 250 psig, the preferred ratio of halide to ammonia is from 1:1.5 to 1:2 and the solvent is present in 2 to 5 times the molar quantity of the halide. The preferred reaction temperature is 200° C. to 220° C. The term halide refers to chloride, bromide or iodide.

Suitable trifluoroethyl halides include the bromide and iodide and especially chloride.

The invention will be further described in the following illustrative examples wherein all parts are by weight unless otherwise expressed.

EXAMPLE 1 (CONTROL)

A 2 liter stainless-steel shaker bomb was evacuated and charged with N-methylpyrrolidone (4.16 moles), trifluoroethyl chloride (3.0 moles) and anhydrous ammonia (7.5 moles). The mixture was heated with shaking for 24 hours at 190°–200° C. The bomb was allowed to cool to room temperature and vented into a dry-ice trap. The bomb was opened and its contents were weighed and analyzed by gas chromatography. Water (500 ml) was added to the contents to dissolve the salts and the mixture was analyzed for iron and fluoride ion content. The results are shown in Table 1 together with data obtained with other solvents.

TABLE 1

| Solvent | Moles Solvent | Moles $CF_3CH_2Cl$ | Moles $NH_3$ | Pressure Max. PSIG | Conversion $CF_3CH_2Cl$, % | Yield % $CF_3CH_2NH_2$ | % Fluoride[b] | Moles Iron |
|---|---|---|---|---|---|---|---|---|
| 2-(2-Ethoxyethoxy)-ethanol | 3.0 | 3.0 | 7.5 | 1600 | 65 | 85 | 0.2 | 0.003 |
| Triethyleneglycol Dimethylether | 2.2 | 3.0 | 7.5 | 1650 | 44 | 72 | 0.2 | 0.005 |
| N—Methylpyrrolidone | 4.2 | 3.0 | 7.5 | 1450 | 96 | 57 | 1.2 | 0.01 |
| N—Methylpyrrolidone Water | 3.8 2.2 | 3.0 | 7.1 | 1200 | 95 | 64 | 0.6 | 0.09 |
| Sulfolane | 4.2 | 3.0 | 7.5 | 1550 | 96 | 44 | 2.5 | 0.01 |
| Water | 22.2 | 3.0 | 7.5 | 1650 | 93 | 72 | 11.2 | 0.15 |

[a]Reaction conditions 190–200° C. for 24 hours
[b]Moles Fluoride Produced/3 Divided by Moles $CF_3CH_2Cl$ Used Table 1 shows that water as solvent results in much iron and fluoride ions, i.e. corrosion. In all instances the pressure was extremely high, exceeding 1000 psig. Sulfolane, in addition to moderate corrosion, also resulted in sulfurous by-products, while N,N-dimethylacetamide (not shown in Table 1) gave major side reactions.

EXAMPLE 2

A 2 liter stainless-steel stirred autoclave was evacuated and charged with N-methylpyrrolidone, trifluoroethyl chloride and anhydrous ammonia. The mixture was stirred and heated as indicated. The mixture was allowed to cool to 120° C. and the products, unreacted starting materials and some solvent were distilled into an evacuated stainless-steel bomb cooled in dry-ice. The reactor was allowed to cool, water (500 ml) was added and the content was analyzed for iron and fluoride content. The crude products in the bomb were introduced into a 1 1 3-necked flask and distilled through a one foot packed column. The data for several runs are shown in Table 2.

TABLE 2

| Moles $NH_3$ | Moles $CF_3CH_2Cl$ | Moles Solvent | Temp. °C. | Maximum Pressure PSIG | Yield % $CF_3CH_2NH_2$ | Yield % $(CF_3CH_2)_2NH$ | Conversion % | Time Hrs. |
|---|---|---|---|---|---|---|---|---|
| 8.1 | 3.0 | 3.3 | 210 | 1320 | 86.8 | 3.0 | 98.7 | 24 |
| 8.1 | 3.0 | 4.2 | 210 | 1200 | 83.7 | 3.3 | 99.5 | 24 |
| 6.0 | 3.0 | 4.2 | 210 | 1050 | 84.3 | 6.1 | 93.7 | 24 |
| 4.5 | 3.0 | 7.5 | 180 | 620 | 78.0 | 9.5 | 84.7 | 24 |
| 2.8 | 1.9 | 7.5 | 180 | 150 | 70.6 | 9.6 | 76.8 | 166 |

Table 2 shows that as the amount of solvent is increased, the pressure is reduced slightly with little effect on conversion or yield. As the amount of ammonia is reduced, the pressure falls markedly, with a concomitant reduction in yield owing to the formation of secondary amine. Temperature has the most significant effect on the pressure but at temperatures much below 175° C. the reaction becomes so slow as to be economically unfavorable.

The last entry in Table 2 gives the details of a run in accordance with the invention.

It will be understood that the specification and examples are illustrative but not limitative of the present invention and that other embodiments within the spirit and scope of the invention will suggest themselves to those skilled in the art.

We claim:

1. In the reaction of a 2,2,2-trifluoroethyl halide with ammonia to produce 2,2,2-trifluoroethylamine, the improvement which comprises effecting the reaction with from about 1 to 3 moles of ammonia per mole of the trifluoroethyl halide at a temperature of about 170° to 240° C. and a pressure less than about 300 psig in the presence of a substantially anhydrous inert solvent present in at least about the same molar amount as the trifluoroethyl halide.

2. A process according to claim 1, wherein the temperature is from about 200° to 220° C.

3. A process according to claim 1, wherein the pressure is at most about 250 psig.

4. A process according to claim 1, wherein the solvent is N-methylpyrrolidone.

5. A process according to claim 1, wherein the solvent is present in at least about 3 times the molar amount of the trifluoroethyl halide.

6. A process according to claim 1, wherein the halide is the chloride.

7. A process according to claim 2, wherein the pressure is at most about 250 psig, the solvent is N-methylpyrrolidone present in at least about 3 times the molar amount of the trifluoroethyl halide, and the halide is the chloride.

* * * * *